United States Patent [19]
Williams

[11] Patent Number: 5,523,118
[45] Date of Patent: Jun. 4, 1996

[54] METHOD OF COATING MICROPOROUS MEMBRANES

[75] Inventor: Gregory D. Williams, Matthews, N.C.

[73] Assignee: Rexam Industries Corporation, Matthews, N.C.

[21] Appl. No.: 312,708

[22] Filed: Sep. 27, 1994

Related U.S. Application Data

[62] Division of Ser. No. 44,296, Apr. 7, 1993.

[51] Int. Cl.⁶ .................... B05D 5/10; B05D 3/12; H05H 1/00
[52] U.S. Cl. .................... 427/208.8; 427/2.31; 427/245; 427/536; 427/356
[58] Field of Search ................ 427/208.8, 2.31, 427/243, 256, 258, 245, 316, 323, 356, 359, 536, 538

[56] References Cited

U.S. PATENT DOCUMENTS

| | | | |
|---|---|---|---|
| Re. 32,991 | 7/1989 | Szycher et al. | 427/2.31 |
| 3,591,010 | 7/1971 | Pall | 210/499 |
| 3,595,732 | 7/1971 | Tingerthal . | |
| 3,622,527 | 11/1971 | Dieterick et al. | 427/245 |
| 3,821,012 | 6/1974 | Lattarulo et al. | 427/245 |
| 3,912,840 | 10/1975 | Edberg | 427/205 |
| 3,914,358 | 10/1975 | Dixon et al. . | |
| 3,968,292 | 7/1976 | Pearman et al. | 427/245 |
| 3,971,315 | 7/1976 | Hansen | 264/46.4 |
| 4,032,440 | 6/1977 | Yasuda . | |
| 4,163,822 | 8/1979 | Walter | 428/304 |
| 4,171,390 | 10/1979 | Hilterhaus et al. | 427/209 |
| 4,172,910 | 10/1979 | Rotar | 427/243 |
| 4,298,666 | 11/1981 | Taskier . | |
| 4,460,371 | 7/1984 | Abber . | |
| 4,485,087 | 11/1984 | Otsuka et al. | 427/2.31 |
| 4,564,010 | 1/1986 | Coughlan et al. | 128/156 |
| 4,567,097 | 1/1986 | Yazaki et al. | 428/317.7 |
| 4,573,996 | 3/1986 | Kwiatek et al. | 604/897 |
| 4,636,424 | 1/1987 | Amemiya et al. . | |
| 4,652,466 | 3/1987 | Thoma et al. | 427/356 |
| 4,661,099 | 4/1987 | von Bittera et al. | 427/208.2 |
| 4,699,792 | 10/1987 | Nick et al. | 424/446 |
| 4,743,249 | 5/1988 | Loveland | 424/447 |
| 4,751,133 | 6/1988 | Szycher et al. | 427/2.31 |
| 4,797,284 | 1/1989 | Loper et al. | 424/449 |
| 4,798,201 | 1/1989 | Rawlings et al. | 128/156 |
| 4,863,788 | 9/1989 | Bellairs et al. . | |
| 4,880,633 | 11/1989 | Loper et al. . | |
| 4,882,377 | 11/1989 | Sweet et al. . | |
| 4,898,734 | 2/1990 | Mathiowitz et al. . | |
| 4,904,475 | 2/1990 | Gale et al. | 424/449 |
| 4,931,281 | 6/1990 | Kim et al. . | |
| 4,951,657 | 8/1990 | Pfister et al. . | |
| 4,956,181 | 9/1990 | Bayer et al. | 424/448 |
| 4,983,395 | 1/1991 | Chang et al. | 424/448 |
| 4,994,278 | 2/1991 | Sablotsky et al. . | |
| 5,008,110 | 4/1991 | Benecke et al. | 424/448 |
| 5,032,403 | 7/1991 | Sinnreich | 424/448 |
| 5,045,354 | 9/1991 | Feimer et al. . | |
| 5,049,417 | 9/1991 | Tsubota et al. | 427/208.8 |
| 5,069,909 | 12/1991 | Sharma et al. . | |
| 5,124,157 | 6/1992 | Colley et al. . | |
| 5,128,124 | 7/1992 | Fankhauser et al. . | |
| 5,130,205 | 7/1992 | Vu et al. . | |
| 5,176,939 | 1/1993 | Shepherd | 427/208.8 |
| 5,198,064 | 3/1993 | Tani et al. | 427/243 |
| 5,266,391 | 11/1993 | Donato et al. . | |
| 5,294,342 | 3/1994 | Donato . | |
| 5,294,346 | 3/1994 | Donato et al. . | |
| 5,296,222 | 3/1994 | Petersen et al. . | |
| 5,322,729 | 6/1994 | Heeter et al. | 427/243 |
| 5,425,865 | 6/1995 | Singleton et al. | 427/243 |
| 5,443,727 | 8/1995 | Gagnon | 210/500.42 |

FOREIGN PATENT DOCUMENTS

| | | |
|---|---|---|
| WO9204987 | 4/1992 | WIPO . |
| WO9303693 | 3/1993 | WIPO . |

*Primary Examiner*—Diana Dudash
*Attorney, Agent, or Firm*—Bell, Seltzer, Park & Gibson

[57] ABSTRACT

A microporous membrane structure is disclosed that comprises a microporous membrane formed of a synthetic polymer and a substantially continuous porous coating on the membrane. The coating is formed from a urethane-based polymer, and provides a permeable barrier that does not interfere with the function of the membrane, and which will prevent further materials that are applied to or adjacent the membrane from interfering with the function of the membrane when those further materials are applied to the porous coating.

6 Claims, 4 Drawing Sheets

METHOD OF COATING MICROPOROUS MEMBRANES

This application is a divisional of application Ser. No. 044,296, filed Apr. 7, 1993.

FIELD OF THE INVENTION

The present invention relates to microporous membranes and in particular relates to a method of coating microporous membranes prior to applying the membrane to a surface or bringing the membrane into contact with a particular material. The coating improves the performance of the membrane in applications such as transdermal drug delivery patches.

BACKGROUND OF THE INVENTION

Microporous membranes, also referred to in the art as semipermeable membranes, are generally continuous structures, often in sheet form, of polymeric material with defined pore sizes. Depending upon the pore size, the membrane will retain bacteria, colloids, and particulates above a relatively small size; e.g. 0.1 micron ($\mu$) in diameter. Such species are either retained on the membrane surface, or trapped in its substructure.

Microporous membranes are used in a wide variety of technical applications. For example, membranes with typical pore sizes of approximately 12 $\mu$ can be used for general clarification, filtration, and identification of large microorganisms. Membranes with smaller pore sizes such as 5 $\mu$ can be used in exfoliative cytology, chemotaxis, gravimetric amount analysis, gross particulate analysis of corrosive fluids, and cytologic evaluation of body fluids such as cerebrospinal fluid. Membranes with pore sizes such as 0.4 $\mu$ can be used for biological analysis of fluids, sterility testing, dewatering and purification of cellular suspensions, and immunology studies. As a final example, membranes with pore sizes as low as 0.1 $\mu$ or smaller can be used for filtration separation of viruses and proteins.

Other uses include humidification, chemical analysis, controlled release systems, electrochemical applications such as battery separators, capacitors and battery vents, industrial processes such as metal recovery, oil-water emulsion processing, protective clothing, ground water purification, packaging, liquid defoaming, fiber optics, composites processing, and information storage.

Other uses include "phase contacting" applications in which the membranes form the functional components of liquid-liquid extraction systems and gassing/degassing processes. For example, in liquid-liquid extraction, a membrane can help extract or transfer a component from one liquid to another without mixing the two liquids.

In yet other applications, microporous membranes form the functional core for sophisticated filtration systems, for supporting plant tissue cultures, for vacuum bag processing of structural composites, and for protective clothing. An example of this last category includes combat uniforms that can protect their wearers from chemical and biological warfare agents.

In almost all such applications, the membrane is placed against one surface, and usually between two surfaces, and serves the function of controlling the movement of some substance either to, from, or between those surfaces, depending upon the particular situation. As might be expected, there exists some circumstances in which the membrane and the surfaces are less compatible than would otherwise be desirable. Alternatively, the nature and function of the overall device structure may require that the membrane be bonded to one or both surfaces using an adhesive. In other circumstances, the membranes, which are often partially formed by a stretching step, are rather fragile in at least one direction, and can benefit from some sort of stabilization, In any case, in order for the membrane to serve its intended purpose, the overall structure and composition of any device into which the membrane is incorporated should avoid interfering with the membrane's character and desired function.

An illustrative and widely growing use of microporous membranes is their incorporation in transdermal (through the skin) drug delivery systems; i.e. the transdermal patch. Generally speaking, transdermal drug delivery systems are used to deliver drugs to and through-the skin or mucosa of a wearer as a means of providing continuous, controlled administration of the drug. Transdermal delivery attempts to avoid the uncertainties of oral administration in which the pharmaceutical compound of interest may not be tolerated by the digestive tract, or in which larger dosages are given on a periodic basis in an attempt to have the body moderate the dosage between administrations. Related problems occur when injecting pharmaceuticals, compounded by the fact that most persons find needles unpleasant and may tend to avoid properly taking their doses on that basis, and that injections must often be given in a physician's office or other such setting.

A transdermal system attempts to avoid these problems by keeping a particular amount of a drug in a reservoir device having a size, shape and appearance similar to a common stick-on bandage. In addition to a drug-containing reservoir, a transdermal drug delivery system usually includes a rate controlling membrane on the side to be placed-against the patient's skin. Microporous membranes are ideal for this purpose. Such a device must also, however, include a means of attaching the membrane to the skin, and the usual technique is to use an adhesive. An adhesive, however, raises its own problems. For example, if the adhesive is incompatible with the microporous membrane, the attachment of the transdermal patch to the patient will be less than satisfactory, especially considering such devices are often worn continuously for a period of several days and must be maintained properly in place throughout the entire period in order to effectively deliver the proper dosage. It is also important that the adhesive remain on the surface of the membrane and that it not fill or block the membrane pores and thus hinder or prevent the delivery system from dispensing the necessary dosage.

Stated differently, the adhesive must keep the membrane in continuous contact with the skin. To do so, the adhesive must anchor properly to both the membrane and the skin without interfering with the membrane's function.

A number of techniques have been suggested for avoiding both problems. For example, in some devices the adhesive is applied to the microporous membrane in a pattern of coated and noncoated areas in order to leave some open areas of the membrane for the medication to pass through. Alternatively, in transdermal patches made in particular shapes, such as a circle, the adhesive is often applied around the perimeter of the patch (e.g. in concentric circles), in yet another attempt to provide the necessary adherence to the skin, while permitting the concurrent necessary transfer of medication through the membrane.

Such techniques raise a number of manufacturing difficulties, as well as generally less than satisfactory performance in the patches themselves. Accordingly, there exists the need for a method-of applying adhesive to a microporous membrane in-a-manner which is convenient, which. permits an appropriate adhesive to be anchored to the membrane, and yet which remains porous so that the membrane can effectively transmit the medication to the patient's skin.

Similar considerations apply to other uses of microporous membranes, such as fluid extraction, solid-liquid filtration, electrochemical applications and barrier fabrics such as in protective clothing.

SUMMARY OF THE INVENTION

The present invention provides a microporous membrane structure that comprises a microporous membrane formed of a synthetic polymer and a substantially continuous porous coating on the membrane. The coating is formed from a urethane-based polymer and provides a permeable barrier that does not interfere with the function,of the membrane. The coating prevents further materials that are applied to or adjacent the membrane from interfering with the function of the membrane when those further materials are applied to the porous coating.

In a particular embodiment, the invention provides a microporous membrane structure that will accept and anchor an adhesive while preventing the adhesive from blocking the pores of the membrane. The membrane structure comprises a microporous membrane formed of a synthetic polymer, and a substantially continuous porous coating on the membrane formed from an adhesive-compatible urethane-based polymer. The coating is carried by the surface of the membrane without-blocking the pores thereof.

The foregoing and other advantages and features of the invention, and the manner in which the same are accomplished, will become more readily apparent upon consideration of the following detailed description of the invention taken in conjunction with the accompanying drawings, which illustrate preferred and exemplary embodiments.

DETAILED DESCRIPTION

The present invention provides a microporous membrane structure that comprises a microporous membrane formed of a synthetic polymer and a substantially continuous porous coating on the membrane. The coating is formed from a urethane-based polymer and provides a permeable barrier that does not interfere with the function of the membrane. The coating prevents further materials that are applied to or adjacent the membrane from interfering with the function of the membrane when those further materials are applied to the porous coating.

As mentioned earlier, microporous membranes have a large number of applications and can be formed in various pore sizes by techniques known by those of ordinary skill in this art. Typical polymers (and types of polymers) for the membrane can include polyolefins, polystyrenes, fluorocarbon polymers, chlorofluorocarbon polymers, polysulfones, polyethersulfones, polyesters, polyacrylates, polycarbonates, polyvinyl chloride, high density polyethylene (HDPE), ultra high molecular weight (UHMW) polyethylene, polypropylene, polyphthalate carbonate, cellulose esters, nitrocellulose, polyvinylidene fluoride, polytetrafluoroethylene (PTFE), nylon 6, and glass. Although a large number of potential polymers is thus listed specifically herein, these are intended to be illustrative of the polymers from which microporous membranes can be selected, and not limiting of them, or of the claimed invention.

Appropriate membrane structures are available from a number of commercial suppliers. These include the "Celgard" membranes from Hoechst Celanese Corporation, Separation Products Division, 13800 South Lakes Drive, Charlotte, N.C. 28217; Porex Technologies, 500 Bohannon Road, Fairburn, Ga. 30213; Nuclepore Corporation, 7035 Commerce Circle, Pleasanton, Calif. 94566; Amicon, Inc., 72 Cherry Hill Drive, Beverly, Mass. 01915; Costar, One Alewife Center, Cambridge, Mass. 02140; Schleicher & Schuell, P.O. Box 12012, Keene, N.H. 03431; and the "Exxaire" Plus nonwoven membranes from Exxon Chemical Company, 750 West Lake Cook Road, Suite 400, Buffalo Grove, Ill., 60089–2069. Again, this list is illustrative rather than limiting, and demonstrates that appropriate microporous membranes consistent with the claims of the present invention can be obtained commercially or otherwise manufactured without undue experimentation.

As also set forth earlier, microporous membranes are available in a wide variety of pore sizes. For example, the membranes available from Nuclepore Corporation referred to above can be obtained commercially with pore sizes as small as 0.015 μ and ranging up to 12 μ. Other materials from other companies have pore sizes ranging up to 350 μ. In the embodiments useful for transdermal drug delivery systems, pore sizes of between about 0.01 μ to 10 μ are often preferred.

Figure 1:
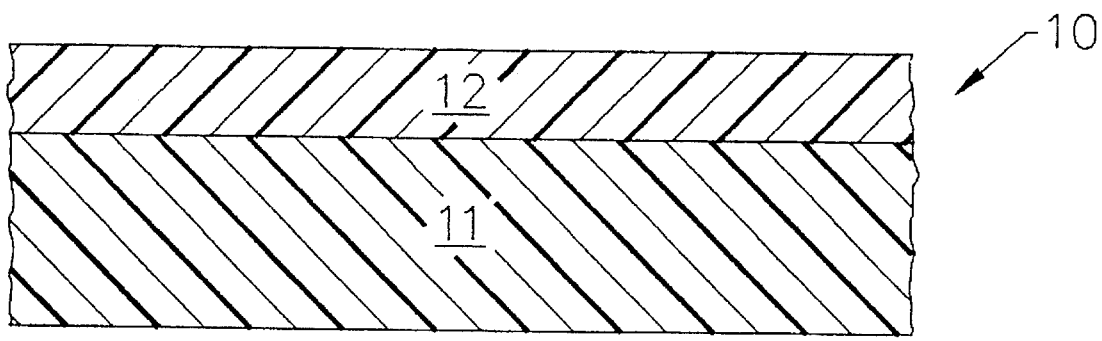
FIG. 1 is a cross sectional view of a membrane coated on one side according to the present invention.

In one specific application, the present invention is a microporous membrane structure that will accept and anchor an adhesive while preventing the adhesive from blocking the pores of the membrane. FIG. 1 illustrates in schematic cross-sectional fashion a membrane structure broadly designated at 10 according to the present invention. The membrane structure 10 includes a microporous membrane 11 formed of a synthetic polymer and a substantially continuous porous coating 12 on the membrane 11 and formed from an adhesive-compatible urethane-based polymer. The coating 12 is carried by the surface of the membrane 11 without blocking the pores of the microporous membrane 11. As discussed further herein, in preferred embodiments of the invention, the coating does not substantially penetrate the membrane. It will be understood that the relative sizes and thicknesses illustrated in FIG. 1 and the other drawings are not drawn to scale, but instead schematically illustrate the various elements of the microporous membrane structure of the invention.

The substantially continuous porous coating 12 on the membrane is preferably formed from an adhesive-compatible urethane-based polymer; i.e. a polymer which provides good anchoring properties between itself and the membrane and between itself and the adhesive. The coating thereby provides an advantageous anchoring element between the membrane 11 and an adhesive. In preferred embodiments, the urethane based polymer comprises an aliphatic or aromatic polycarbonate urethane dispersion, an aliphatic or aromatic polyether urethane dispersion, or an aliphatic or aromatic polyester urethane dispersion. In certain embodiments, the urethane based polymer can be crosslinked, and for urethane based polymers, preferred crosslinking agents include carbodiimide (cyanamide), aziridines, isocyanates, and melamine, or combinations thereof.

As is further known to those familiar with polymer chemistry, polyurethanes are thermoplastic polymers (which can be made more thermosetting with crosslinking) produced by the condensation reaction of a polyisocyanate and a hydroxyl-containing material; e.g. a polyol derived from propylene oxide or trichlorobutylene oxide. Urethanes have high elastic modulus, good electrical resistance, and high moisture proofness. Polyurethane coatings provide an excellent range of available hardness, gloss, flexibility, abrasion resistance, and adhesion, and are resistant to impact, weathering, acids and alkalis, and are only attacked by aromatic or chlorinated solvents.

Figure 2:
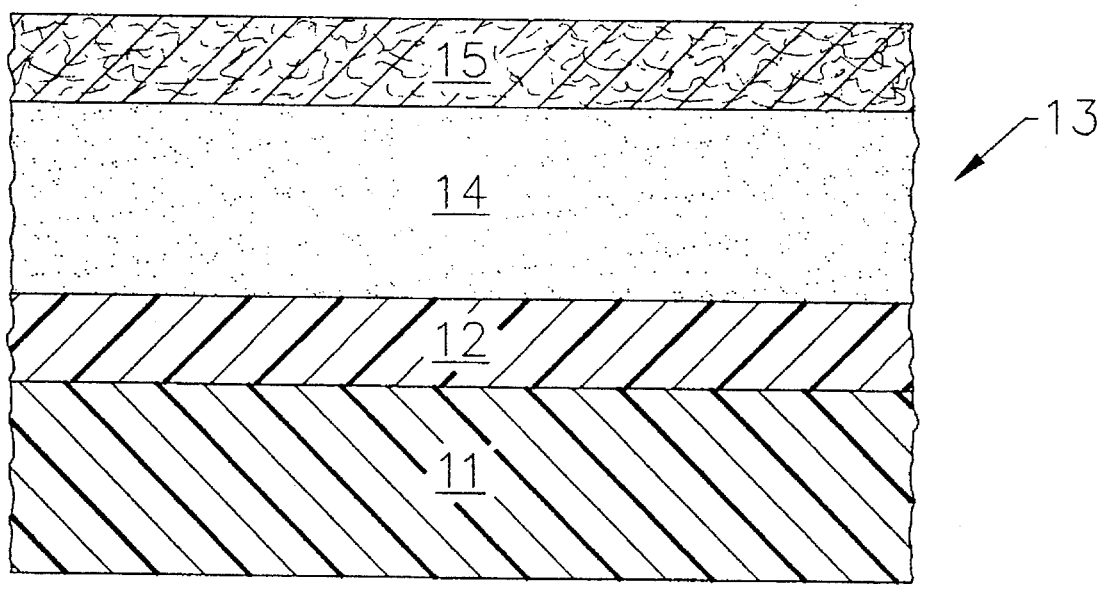
FIG. 2 is a cross sectional view of an adhesive coated membrane structure according to the present invention.

FIG. 2 illustrates a second microporous membrane structure broadly designated at 13 that again includes the microporous membrane 11 and the coating 12 numbered identically with FIG. 1 for purposes of clarity. Additionally, the illustrated membrane structure 13 includes an adhesive layer 14 and a removable release layer 15 on the adhesive layer 14 for providing a cover for the adhesive prior to use of the membrane. Stated differently, the adhesive is most usefully covered with the release layer when the transdermal device is manufactured so that the user can simply remove the release layer (often formed of paper) and then apply the adhesive directly to the skin. Appropriate adhesives should be selected to be compatible with the membrane, the coating, and the surface to which the adhesive is to be applied. Furthermore, in the case of a transdermal patch, the adhesive should be selected to avoid solubility of the medication in the adhesive and so that the adhesive does not provide any obstacle or deterrent of the movement of the drug from the membrane to the skin or other appropriate surface.

In the present invention, the preferred adhesives are selected from the group consisting of acrylic latex, methacrylic latex, polyacrylate, vinyl acetate, ethylene vinyl acetate, polyurethane latex, polyvinyl chloride latex, polyethylene latex, polystyrene latex, acrolamide, methylacrolamide, natural rubbers, synthetic rubbers, silicones, polysyloxanes, and combinations thereof. As used herein, and as known to those familiar with these materials, the term "latex" refers to an aqueous suspension of a hydrocarbon polymer. Latexes occur naturally in some species of trees, shrubs or plants, or they can be made synthetically. Synthetic latexes are generally made by emulsion polymerization techniques from a number of the polymers listed immediately above and in general their particle size is much smaller than a natural latex, 0ranging from 0.05 μ to about 0.15 μ. They thus represent colloidal suspensions.

As in the structures illustrated in FIG. 1 and FIG. 2, the membrane 11 includes the coating 12, which is in turn coated with the adhesive 14, and preferably with the removable release layer 15. As in the earlier described structures, the adhesive-compatible urethane-based coating 12 is preferably selected from the group consisting of aliphatic and aromatic polycarbonate urethanes, aliphatic and aromatic polyether urethane dispersions, and aliphatic and aromatic polyester urethanes. These can be crosslinked to a greater or lesser extent as may be desired using the crosslinking Agents set forth earlier. Similarly, the adhesive is preferably selected from the group set forth above, although this is intended as an illustrative list rather than a limiting one.

In another aspect, the invention comprises the method of coating the microporous membrane to produce the membrane structure that will accept the adhesive without allowing the adhesive to block the pores of the membrane or otherwise interfere with the membrane. The method comprises applying an aqueous dispersion of an adhesive-compatible polyurethane-based polymer to a microporous membrane formed of a synthetic polymer and in an amount sufficient for the dispersion to macroscopically cover the membrane when the dispersion is dry and to prevent an adhesive applied to the dried dispersion from blocking the pores of the microporous membrane, but less than an amount of polyurethane-based polymer that would block the pores of the membrane when dry. Appropriate coating techniques are well known in the art, and can include roll, gravure, die, knife, or rod techniques. In one embodiment, a coating amount of about two (2) pounds per ream is appropriate, and produces a coating of about 0.05 mil in thickness.

Following its application, the aqueous dispersion is dried sufficiently to substantially remove the water and any other solvents present in the dispersion, to produce cross-linking where desired, and to produce a dry, stable layer on the microporous membrane. A preferred drying step comprises drying the dispersion at about 150° F. for between about two and three minutes.

As presently best understood, when the aqueous dispersion is applied, the dispersed particles are large enough to avoid entering the membrane's pores, and thus they avail blocking the membrane. As the dispersion dries, the particles coalesce into a substantially continuous film that likewise-avoids filching the pores, or otherwise blocking the membrane.

Preferably, the polyurethane for the coating is chemically modified in known fashion to enhance the performance of the dispersion. Preferred dispersions have particle sizes of between about 0.01 μ and 0.1 μ and are typically white, clear, or translucent emulsions with a viscosity of about 50–10,000 centipoise.

For example, one appropriate coating is the UE-40-350 coating from ICI (ICI United States, Inc., Wilmington Del. 19897) marketed under the "Permuthane" designation. Another related and preferred coating is the UE-40-512 (polyether urethane) Permuthane coating also available from ICI. These coatings are soft, lightfast, water borne polycarbonate urethane dispersions. The dispersions form soft, glossy films, have excellent hydrolysis resistance, outstanding long term weathering, and provide excellent flexibility and adhesion to a wide variety of substrates including various polymers.

In applying the aqueous dispersion to the microporous membrane, the surface of the microporous membrane to which the dispersion is applied is preferably corona treated prior to applying the dispersion. Corona treatment is an electrical discharge treatment which appears to increase the functionality (i.e. number of available functional groups) on the surface of a polymer, probably by slightly oxidizing the surface, to thereby provide better adhesion between the polymer and the other materials coated upon it.

Consistent with the structures disclosed earlier, the method of the invention can further comprise the step of applying an adhesive to the dried polyurethane-based polymer on the membrane, and the step of applying an adhesive preferably comprises applying an adhesive from the group described earlier.

Figure 3:
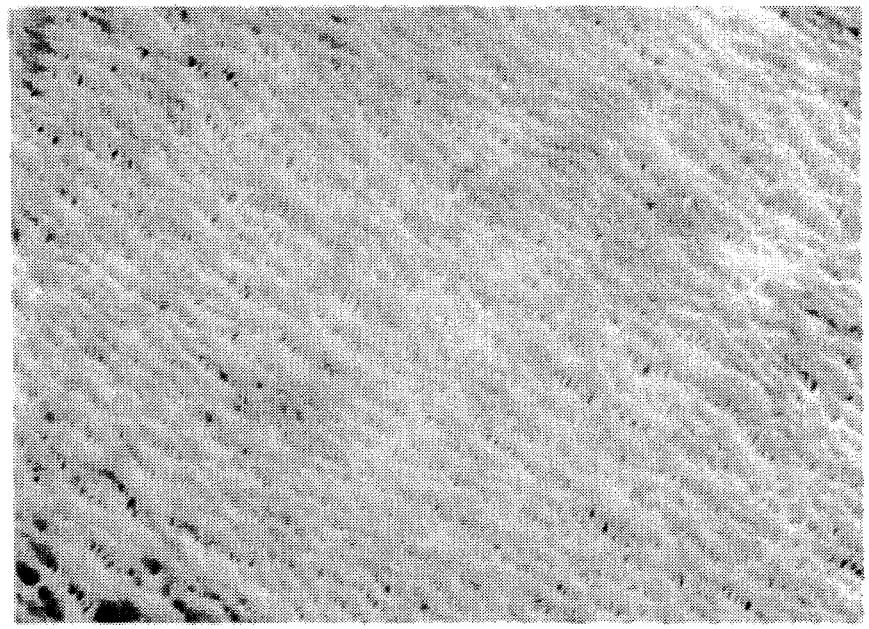
FIG. 3 is a scanning electron micrograph (SEM) of an uncoated semipermeable membrane taken at a magnification of 5710X.
Figure 4:
FIG. 4 is a scanning electron micrograph of a semipermeable membrane coated according to the invention and taken at a magnification of 5600X.

The invention is further illustrated in FIGS. 3 through 8 which are signaling electron micrographs (SEM). FIG. 3 illustrates a microporous membrane obtained from Hoechst Celanese Corporation under the "Celgard" trademark as seen under a magnification of 5710X. FIG. 4 is taken at 5600X and illustrates the appearance of the same surface of the membrane shown in FIG. 3 when coated with the a polyurethane-based coating and applied according to the present invention. FIG. 4 manifests the continuous appearance of the coated surface compared to the uncoated surface in FIG. 3.

Figure 5:
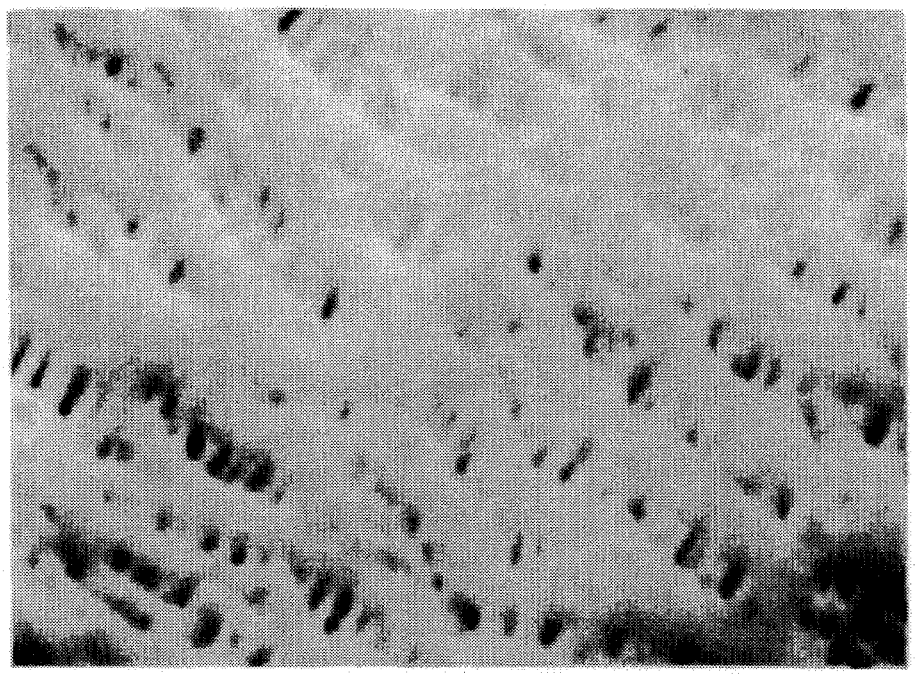
FIG. 5 is a scanning electron micrograph of an uncoated semipermeable membrane taken at a magnification of 23,200X.
Figure 6:
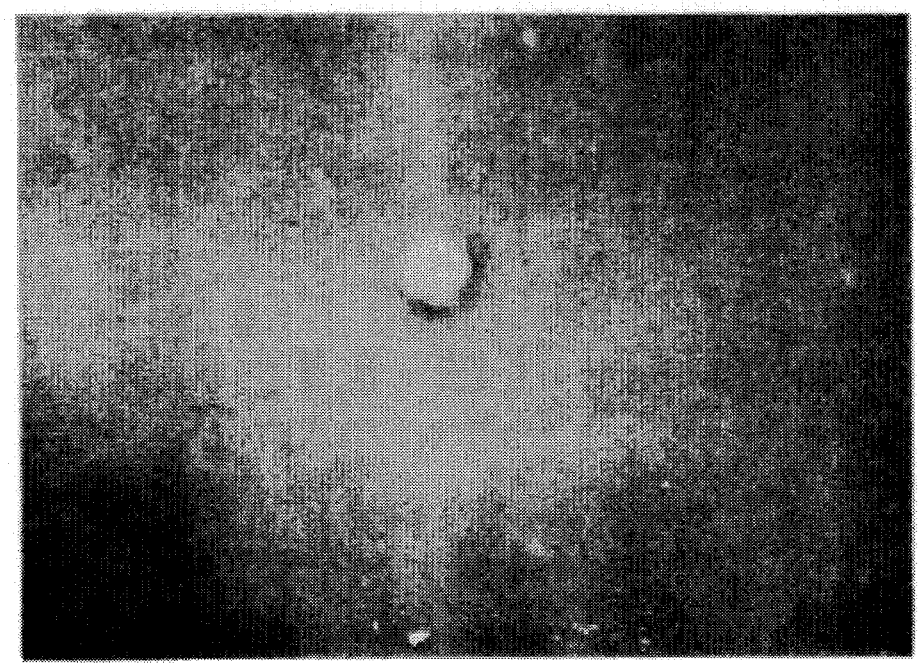
FIG. 6 is a scanning electron micrograph of a semipermeable membrane coated according to the invention and taken at a magnification of 22,700X.

FIG. 5 is a more highly magnified view of the membrane of the SEM of FIG. 3, and taken at 23,200ZX. Similarly, FIG. 6 is a more magnified view of the coated membrane of FIG. 4 taken at 22,700X. FIG. 6 further illustrates, particularly at this higher magnification level, the surface obtained using the present invention.

Figure 7:
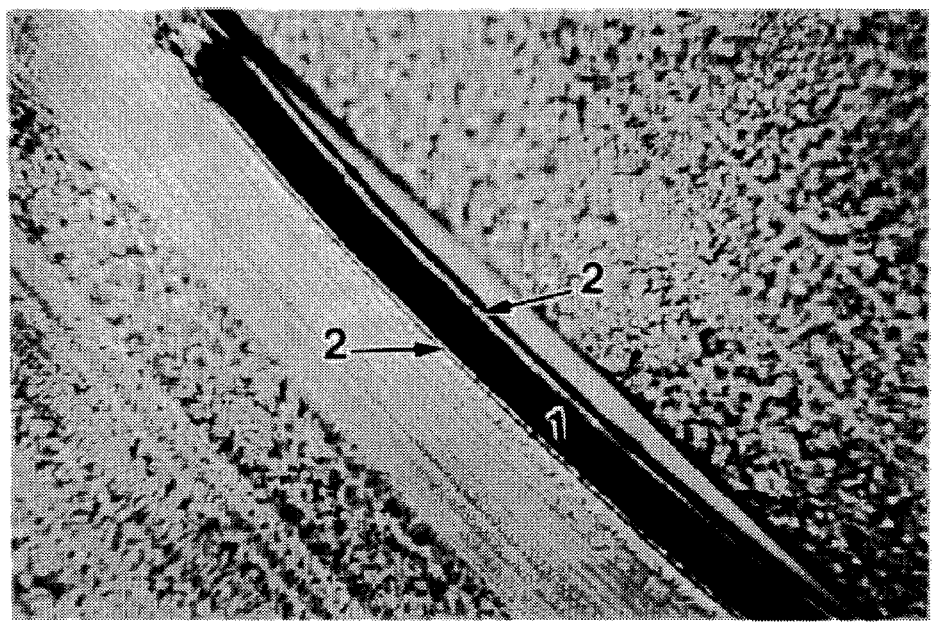
FIGS. 7 and 8 are scanning electron micrographs taken along a cross section of a microporous membrane coated according to the present invention and at magnification of 160X.
Figure 8:
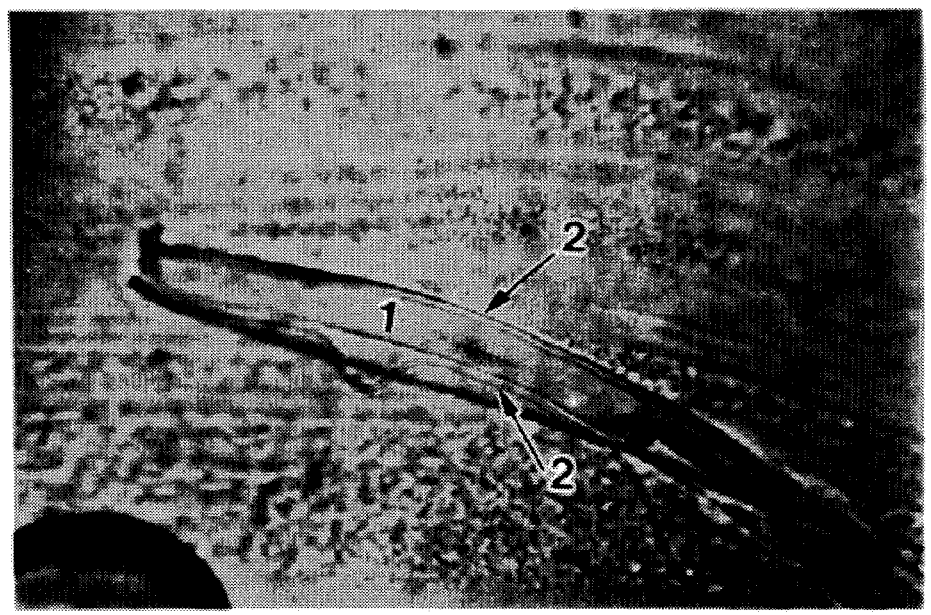

FIGS. 7 and 8 are cross-sectional views in which the coated semipermeable membrane according to the invention was mounted in epoxy in order to provide a structural base, and then scanned at a magnification of 160X. In FIG. 7 the membrane is designated at 1 and the polyurethane-based coating at 2. FIG. 8 is a cross-sectional view of a membrane mounted and photographed in a manner identical to FIG. 7, but with the pores of the membrane filled with immersion oil.

These cross-sectional views reveal a dual layer base having a total thickness of approximately 25 μ. The polyurethane coatings on either side of the microporous membrane measure approximately 3–4 μ and 6–7 μ respectively. The coating of the invention is distinctly visible in both SEMs as the layers 2 on the membrane and demonstrates that the coating of the invention advantageously avoids entering or filling the membrane pores. In FIG. 7, the microporous membrane appears dark because of the presence of the pores. When the pores are filled with immersion oil (FIG. 8), the appearance of the membrane becomes more transparent. In this regard, the penetration of the oil through the coating and into the membrane confirms that the polyurethane coating did not block the membrane pores.

FIGS. 7 and 8 demonstrate that in certain embodiments, the sheet-like membrane can be coated on both sides.

The porosity of the coated membrane structure of the invention can be confirmed in any appropriate manner. As known to those of skill in this art, typical techniques include measuring the rate of gas or liquid diffusion (or flow) through the coated membrane, or a water bubble point. Standard techniques include ASTM D-726, Method B; ASTM E96-66 Procedures A and BW; and ASTM D-2873. Additionally, ASTM D-792 describes the method for measuring the density of the membrane by liquid displacement, and ASTM E96-80 describes methods for measuring a membrane's water vapor transmission rate.

As stated earlier, the coated membrane of the present invention can be used in a variety of applications: filtration, liquid-liquid extraction, gassing/degassing processes, electrochemical systems, and protective fabrics.

Thus, in another embodiment, the invention comprises a method of extracting a component from a first fluid into a second fluid, the fluids being gases or liquids, while avoiding direct contact of the fluids by placing, for a time sufficient to obtain a desired degree of extraction, each respective fluid into contact with opposite sides of a microporous membrane formed of a synthetic polymer, and through which membrane the component will pass, but the respective fluids will not. The membrane includes a substantially continuous porous coating on at least one side, the coating being formed-from a urethane-based polymer as described herein that provides a permeable barrier that does not interfere with the function of the membrane, and which will prevent the respective fluids from interfering with the function of the membrane when the respective fluids are applied to the porous coating.

In yet another embodiment, the invention comprises a method of filtering a solid from a mixture of the solid and a liquid by forcing a mixture of the solid and the liquid through a microporous membrane formed of a synthetic polymer with a substantially continuous porous coating on the membrane, the coating being formed from the urethane-based polymer described herein. As in other embodiments, the coating provides a permeable barrier that does not interfere with the function of the membrane, and prevents the solid the liquid in the mixture from interfering with the function of the membrane when the mixture is forced through the coated membrane.

In a further embodiment the invention comprises an electrochemical cell in which the anode and cathode are separated by the microporous membrane formed of a synthetic polymer, and in Which the membrane is coated on at least one surface thereof with the substantially continuous porous coating formed from a urethane-based polymer as described herein. The coating provides a permeable barrier that does not interfere with the function of the membrane, and which will prevent the cell electrolytes or other materials that are applied to or in contact with the membrane from interfering with the function of the membrane.

In another exemplary embodiment, the invention comprises an article of protective clothing having at least one layer formed of a microporous membrane formed of a synthetic polymer, and a substantially continuous porous coating on the membrane. The coating is formed from the urethane based polymer described herein, and provides a permeable barrier that does not interfere with the function of the membrane, and which will prevent fabrics or other materials that are applied to or adjacent the membrane from interfering with the function of the membrane.

In the drawings and specification, there have been disclosed typical preferred embodiments of the invention and, although specific terms have been employed, they have been used in a generic and descriptive sense only and not for purposes of limitation, the scope of the invention being set forth in the following claims.

That which is claimed is:

1. A method of coating a microporous membrane to produce a membrane structure that will accept and anchor an adhesive without allowing the adhesive to block the pores of the membrane or otherwise interfere with the membrane, the method comprising:

applying a macroscopically continuous coating of an aqueous dispersion of an adhesive-compatible polyurethane polymer to a microporous membrane formed of a synthetic polymer, and in an amount sufficient for the polyurethane polymer coating to macroscopically cover the membrane when dry but less than an amount of polyurethane-based polymer that would block the pores of the membrane when the coating is dry;

drying the coating sufficiently to substantially remove the water and any other solvents present in the dispersion, to promote cross-linking and curing, and to produce a dry stable porous layer of polyurethane polymer on the microporous membrane; and applying an adhesive to the porous layer of polyurethane polymer on the microporous membrane.

2. A method according to claim 1 and further comprising the step of corona treating the surface of the microporous membrane to which the dispersion is applied prior to the step of applying the dispersion.

3. A method according to claim 1 wherein said adhesive is selected from the group consisting of: acrylic latex, methacrylic latex, polyacrylate, vinyl acetate, ethylene vinyl acetate, polyurethane latex, polyvinyl chloride latex, polyethylene latex, polystyrene latex, acrylamide, methylacrylamide, natural rubbers, synthetic rubbers, silicones, polysiloxanes, and combinations thereof.

4. A method according to claim 1 wherein the step of drying the aqueous dispersion comprises drying the dispersion at 150° F. for between about 2 and 3 minutes.

5. A method according to claim 1 wherein the step of applying the polyurethane polymer comprises applying the polymer using a method selected from the group consisting of: roll coating, gravure coating, die coating, knife coating, and Meyer rod coating.

6. A method according to claim 1 wherein the step of applying the polyurethane polymer comprises applying the polymer in a thickness of about 0.05 mil.

* * * * *